(12) United States Patent
Sims et al.

(10) Patent No.: US 11,304,743 B2
(45) Date of Patent: Apr. 19, 2022

(54) ELECTROSURGICAL FORCEPS

(71) Applicant: COVIDIEN LP, Mansfield, MA (US)

(72) Inventors: Grant T. Sims, Boulder, CO (US);
Kelley D. Goodman, Erie, CO (US);
Craig V. Krastins, Arvada, CO (US);
Robert F. Mccullough, Jr., Boulder, CO (US); Jennifer L. Rich, Parker, CO (US); Daniel W. Mercier, Erie, CO (US)

(73) Assignee: Covidien LP, Mansfield, MA (US)

( * ) Notice: Subject to any disclaimer, the term of this patent is extended or adjusted under 35 U.S.C. 154(b) by 528 days.

(21) Appl. No.: 16/261,759

(22) Filed: Jan. 30, 2019

(65) Prior Publication Data

US 2020/0237433 A1 Jul. 30, 2020

(51) Int. Cl.
*A61B 18/14* (2006.01)
*A61B 18/00* (2006.01)

(52) U.S. Cl.
CPC ...... *A61B 18/1445* (2013.01); *A61B 2018/00172* (2013.01); *A61B 2018/00916* (2013.01); *A61B 2018/1455* (2013.01)

(58) Field of Classification Search
CPC ...... A61B 18/1445; A61B 2018/00172; A61B 2018/00916; A61B 2018/1455
See application file for complete search history.

(56) References Cited

U.S. PATENT DOCUMENTS

| | | | |
|---|---|---|---|
| 5,219,354 A | 6/1993 | Choudhury et al. | |
| 5,447,265 A | 9/1995 | Vidal et al. | |
| 5,499,997 A | 3/1996 | Sharpe et al. | |
| 5,797,938 A | 8/1998 | Paraschac et al. | |
| 5,860,975 A | 1/1999 | Goble et al. | |
| 6,603,100 B2 | 8/2003 | Wilkins et al. | |
| 7,207,472 B2 | 4/2007 | Wukusick et al. | |
| 7,297,136 B2 | 11/2007 | Wyrick | |
| 7,550,975 B2 | 6/2009 | Honda et al. | |
| 7,819,299 B2 | 10/2010 | Shelton, IV et al. | |
| 8,197,479 B2 | 6/2012 | Olson et al. | |
| 8,343,151 B2 | 1/2013 | Siebrecht et al. | |
| 8,388,646 B2 | 3/2013 | Chojin | |
| 8,480,671 B2 | 7/2013 | Mueller | |
| 8,568,412 B2 | 10/2013 | Brandt et al. | |
| 8,628,557 B2 | 1/2014 | Collings et al. | |
| 8,679,115 B2 | 3/2014 | Reschke | |
| 8,696,665 B2 | 4/2014 | Hunt et al. | |
| 8,752,264 B2 | 6/2014 | Ackley et al. | |
| 8,920,461 B2 | 12/2014 | Unger et al. | |
| 8,968,313 B2 | 3/2015 | Larson | |
| 8,973,805 B2 | 3/2015 | Scirica et al. | |
| 9,345,534 B2 | 5/2016 | Artale et al. | |

(Continued)

FOREIGN PATENT DOCUMENTS

| | | |
|---|---|---|
| DE | 102010013060 A1 | 9/2011 |
| DE | 202012013219 U1 | 11/2015 |
| WO | 2009153015 A1 | 12/2009 |

*Primary Examiner* — Michael F Peffley
*Assistant Examiner* — Bo Ouyang

(57) ABSTRACT

An electrosurgical forceps includes a pair of first and second shaft members pivotably coupled to one another, an end effector assembly coupled to the pair of first and second shaft members, a knife, and a biasing member. The biasing member is disposed about the knife and configured to resiliently bias the knife toward a retracted position.

17 Claims, 3 Drawing Sheets

(56) References Cited

U.S. PATENT DOCUMENTS

| | | |
|---|---|---|
| 9,610,114 B2 | 4/2017 | Baxter, III et al. |
| 9,675,405 B2 | 6/2017 | Trees et al. |
| 9,707,029 B2 | 7/2017 | Nobis et al. |
| 9,877,775 B2 | 1/2018 | Hart |
| 2001/0045442 A1 | 11/2001 | Whitman |
| 2003/0199869 A1* | 10/2003 | Johnson ............ A61B 18/1445 606/50 |
| 2004/0094597 A1 | 5/2004 | Whitman et al. |
| 2006/0079891 A1* | 4/2006 | Arts ................... A61B 18/1442 606/51 |
| 2007/0043352 A1 | 2/2007 | Garrison et al. |
| 2007/0173814 A1 | 7/2007 | Hixson et al. |
| 2007/0179499 A1* | 8/2007 | Garrison ............ A61B 18/1445 606/51 |
| 2010/0286691 A1 | 11/2010 | Kerr et al. |
| 2011/0054468 A1 | 3/2011 | Dycus |
| 2012/0197253 A1 | 8/2012 | Nishimura et al. |
| 2012/0265241 A1 | 10/2012 | Hart et al. |
| 2013/0296843 A1 | 11/2013 | Boudreaux et al. |
| 2014/0005704 A1 | 1/2014 | Vakharia et al. |
| 2014/0276738 A1 | 9/2014 | Price et al. |
| 2014/0276970 A1 | 9/2014 | Messerly et al. |
| 2014/0309665 A1 | 10/2014 | Parihar et al. |
| 2015/0272660 A1 | 10/2015 | Boudreaux et al. |
| 2016/0135868 A1 | 5/2016 | Joseph et al. |
| 2016/0157922 A1* | 6/2016 | Lee ................... A61B 18/1442 606/51 |
| 2016/0166256 A1 | 6/2016 | Baxter, III et al. |
| 2017/0196629 A1 | 7/2017 | Nagtegaal |
| 2017/0238991 A1 | 8/2017 | Worrell et al. |
| 2017/0245933 A1 | 8/2017 | Graham et al. |
| 2017/0367752 A1 | 12/2017 | Boudreaux et al. |

* cited by examiner

ELECTROSURGICAL FORCEPS

BACKGROUND

The present disclosure relates to electrosurgical instruments and, more particularly, to electrosurgical forceps for grasping, treating, and/or dividing tissue.

TECHNICAL FIELD

A surgical forceps is a plier-like instrument which relies on mechanical action between its jaws to grasp tissue. Electrosurgical forceps utilize both mechanical clamping action and electrical energy to treat tissue, e.g., coagulate, cauterize, and/or seal tissue.

Typically, once tissue is treated, the surgeon accurately severs the treated tissue. Accordingly, many electrosurgical forceps have been designed which incorporate a knife configured to effectively sever tissue after treating the tissue.

SUMMARY

As used herein, the term "distal" refers to the portion that is being described which is further from a surgeon, while the term "proximal" refers to the portion that is being described which is closer to a surgeon. Further, to the extent consistent, any of the aspects described herein may be used in conjunction with any or all of the other aspects described herein.

As used herein, the terms parallel and perpendicular are understood to include relative configurations that are substantially parallel and substantially perpendicular up to about +/−10 degrees from true parallel and true perpendicular.

An electrosurgical forceps provided in accordance with aspects of the present disclosure includes a pair of first and second shaft members pivotably coupled to one another, an end effector assembly coupled to the pair of first and second shaft members and configured to move between an open configuration and a closed configuration in response to pivoting of the first and second shaft members, a knife selectively translatable through the first shaft member from a retracted position to an extended position in which the knife extends at least partially through the end effector assembly, and a biasing member disposed around the knife and configured to resiliently bias the knife toward the retracted position.

In aspects, the biasing member may be an elongated spring wrapped about the knife.

In some aspects, the biasing member may be compressed between a wall of the knife and a portion of the first or second shaft members during distal translation of the knife toward the extended position.

In further aspects, the wall may be a stop configured to resist distal translation of the knife beyond the extended position.

In other aspects, the biasing member may have a proximal end portion configured to be distally urged by the wall of the knife during distal translation of the knife, and a distal end portion configured to engage the portion of the first or second shaft members during distal translation of the knife.

In aspects, the forceps may further include a knife deployment mechanism including a linkage having a proximal end portion operably coupled to a trigger, and a pivot pin rotatably supported by a distal end portion of the linkage and coupled to the knife. The knife may be configured to move between the retracted and extended positions in response to an actuation of the trigger.

In some aspects, the knife deployment mechanism may include a crank having a first end portion coupled to the trigger and a second end portion rotatably coupled to the proximal end portion of the linkage.

In other aspects, the crank may rotate in response to an actuation of the trigger to rotate and translate the linkage.

In accordance with an aspect of the present disclosure, an electrosurgical forceps is provided and includes a pair of first and second shaft members pivotably coupled to one another, a trigger rotatably supported by at least one of the first or second shaft members, an end effector assembly coupled to the pair of first and second shaft members and configured to move between an open configuration and a closed configuration in response to pivoting of the first and second shaft members, a knife selectively translatable through the first shaft member from a retracted position to an extended position in which the knife extends at least partially through the end effector assembly, a knife deployment mechanism including a crank having a first end portion coupled to the trigger and a second end portion operably coupled to the knife, and a biasing member coupled to the trigger and configured to resiliently bias the knife toward the retracted position.

In aspects, the biasing member may have a first end portion attached to the trigger and a second end portion fixed to a portion of at least one of the first or second shaft members.

In some aspects, the first shaft member may have an outer housing and an inner frame disposed within and axially fixed relative to the outer housing. The trigger may be rotatably supported by the inner frame.

In further aspects, the second end portion of the biasing member may be fixed to the inner frame.

In other aspects, the biasing member may be a torsion spring.

In aspects, the knife deployment mechanism may include a linkage having a proximal end portion operably coupled to the trigger. The knife may be configured to move between the retracted and extended positions in response to an actuation of the trigger.

In some aspects, the knife deployment mechanism may include a pivot pin rotatably supported by a distal end portion of the linkage and coupled to the knife.

In other aspects, the crank may rotate in response to an actuation of the trigger to rotate the linkage and move the knife between the retracted and extended position.

BRIEF DESCRIPTION OF THE DRAWINGS

Various aspects and features of the present disclosure are described hereinbelow with reference to the drawings wherein like numerals designate identical or corresponding elements in each of the several views.

DETAILED DESCRIPTION

Figure 1:
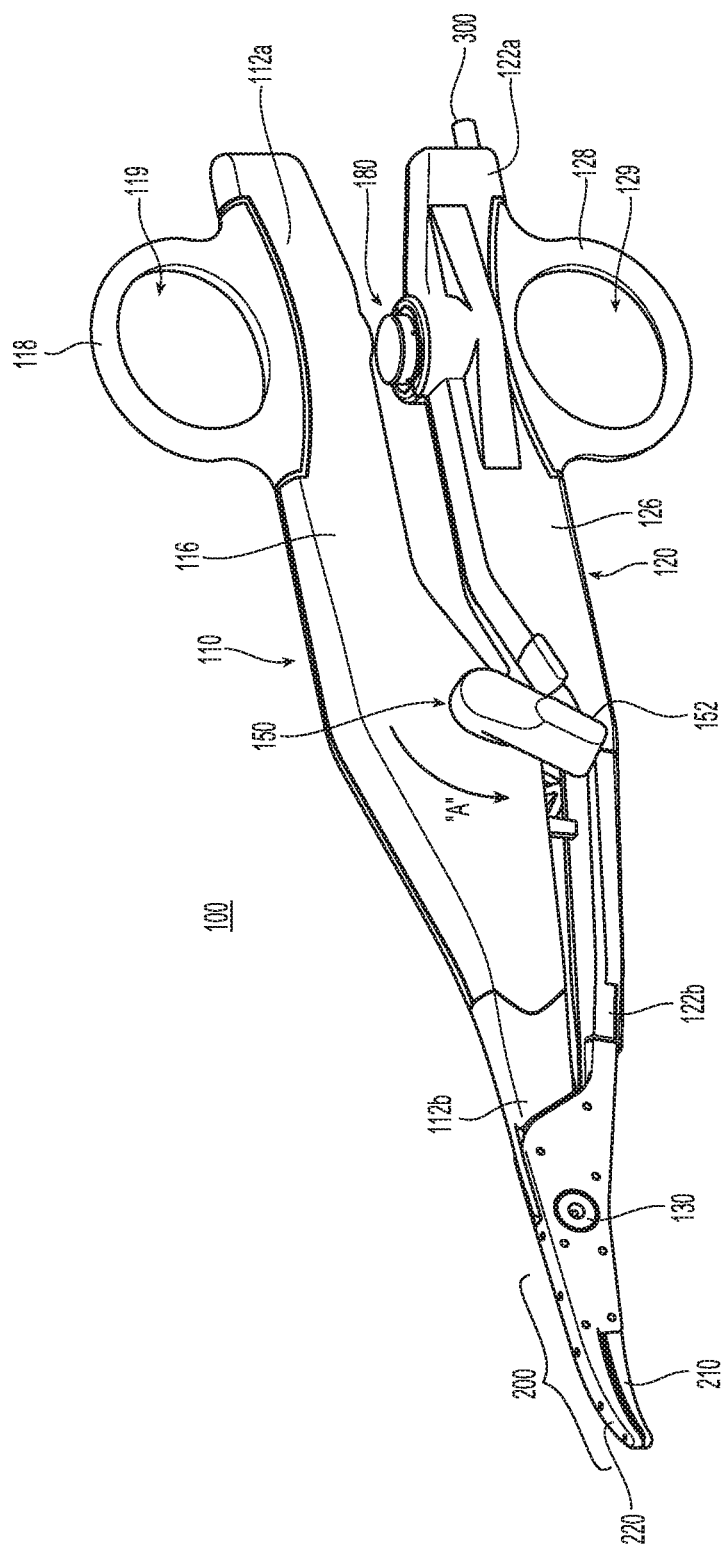
FIG. 1 is a side, perspective view of an electrosurgical forceps provided in accordance with aspects of the present disclosure.
Figure 2:
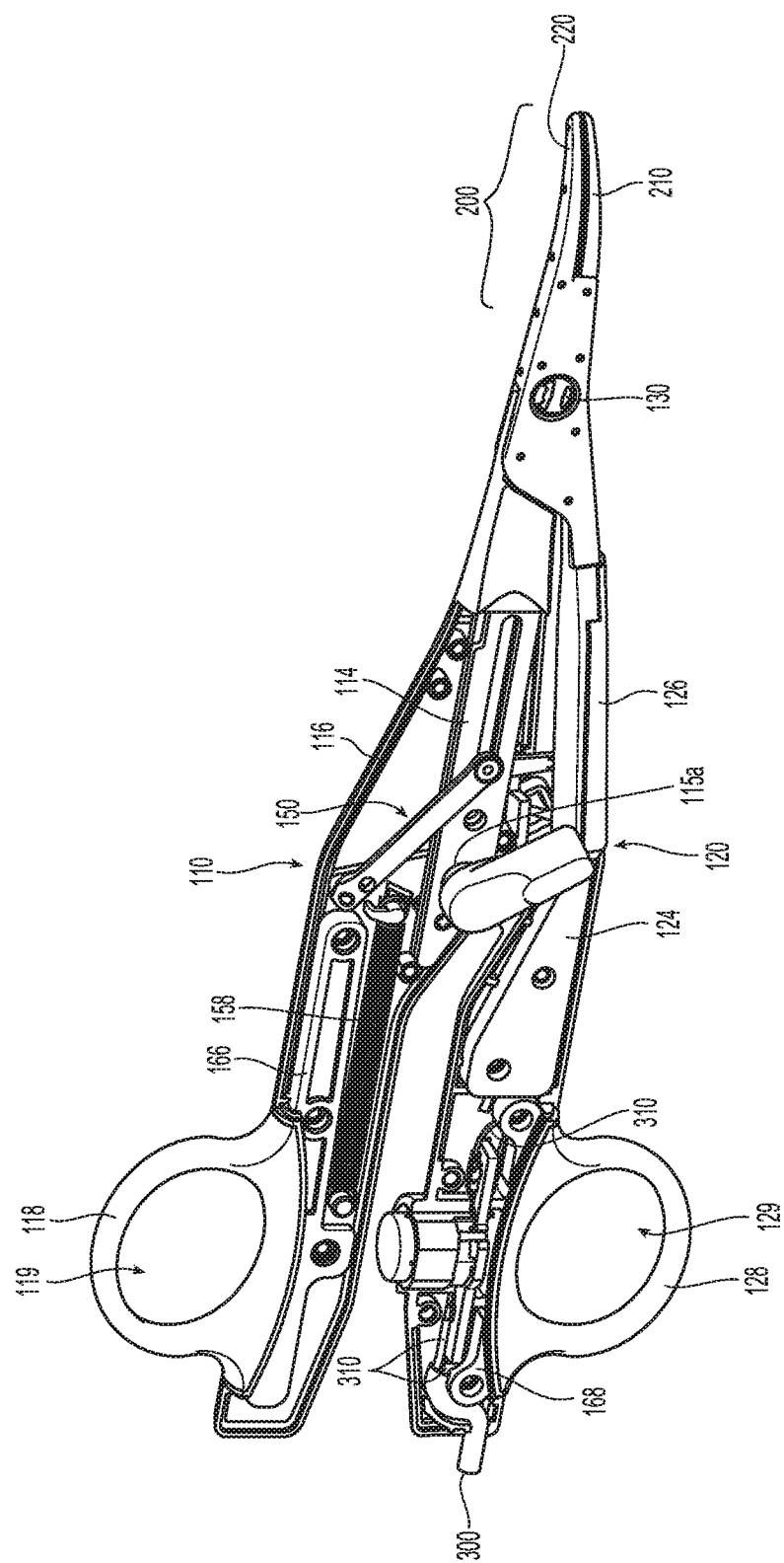
FIG. 2 is a perspective view from one side of the forceps of FIG. 1 with portions of outer housings of first and second shaft members removed to illustrate the internal components therein.

Referring to FIGS. 1 and 2, a forceps 100 provided in accordance with the present disclosure generally includes first and second shaft members 110, 120 and an end effector assembly 200. Shaft members 110, 120 each have a respective proximal end portion 112a, 122a and a respective distal end portion 112b, 122b. End effector assembly 200 includes first and second jaw members 210, 220 extending from distal end portions 112b, 122b of first and second shaft members 110, 120, respectively. Forceps 100 further includes a pivot member 130 pivotably coupling first and second shaft members 110, 120 with one another, a knife 140 (FIG. 3), a knife deployment mechanism 150 for selectively deploying knife 140, and a switch assembly 180 for enabling the selective supply of electrosurgical energy to end effector assembly 200. An electrosurgical cable 300 electrically couples forceps 100 to a source of energy (not shown), e.g., an electrosurgical generator, to enable the supply of electrosurgical energy to jaw members 210, 220 of end effector assembly 200 upon activation of switch assembly 180.

Each shaft member 110, 120 includes an inner frame 114, 124, an outer housing 116, 126 surrounding at least a portion of the respective inner frame 114, 124, and a handle 118, 128 engaged with the respective outer housing 116, 126 towards proximal end portions 112a, 122a of first and second shaft members 110, 120, respectively. Inner frame 124 of second shaft member 120 and inner frame 114 of first shaft member 110 are pivotably coupled to one another via pivot member 130 such that shaft members 110, 120 are movable relative to one another between spaced-apart and approximated positions to thereby pivot jaw members 210, 220 relative to one another between open and closed positions.

Outer housings 116, 126 of first and second shaft members 110, 120 enclose and/or operably support the internal components disposed within first and second shaft members 110, 120. More specifically, outer housing 116 of first shaft member 110 encloses and supports at least a portion of inner frame 114 and knife deployment mechanism 150, while outer housing 126 of shaft member 120 receives electrosurgical cable 300 and encloses and supports at least a portion of inner frame 124, switch assembly 180, and the lead wires 310 of electrosurgical cable 300. Handles 118, 128 are engaged with outer housings 116, 126 towards proximal end portions 112a, 112b of first and second shaft members 110, 120 and extend outwardly from first and second shaft members 110, 120. Handles 118, 128 define finger holes 119, 129 configured to facilitate grasping and manipulating shaft members 110, 120.

Figure 3:
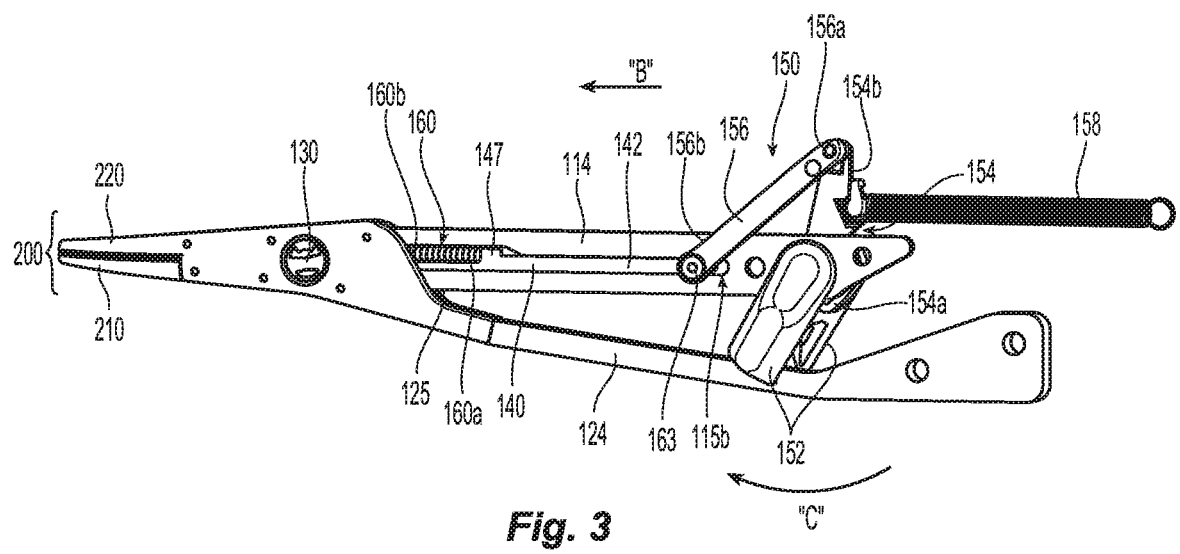
FIG. 3 is a side, perspective view of the forceps of FIG. 1 with portions removed to illustrate a knife and a knife deployment mechanism.

With reference to FIGS. 2 and 3, knife deployment mechanism 150 is coupled to first shaft member 110 and generally includes a pair of opposed triggers 152 extending from either side of first shaft member 110, a crank 154, a linkage 156, and first and second biasing members 158, 160. Knife deployment mechanism 150 is disposed within outer housing 116 of first shaft member 110 with the exception of opposed triggers 152, which extend from either side of outer housing 116. Triggers 152 are rotatably coupled to inner shaft 114 of first shaft member 110 and are typically actuated by fingers of a user. Crank 154 is configured for positioning on one side of inner frame 114 of shaft member 110 and includes a pair of integral (or otherwise engaged) pivot bosses 161a, 161b (FIG. 4) extending from either side thereof at a first end portion 154a of crank 154. A first pivot boss 161a of crank 154 extends through a trigger aperture 115a defined in inner frame 114 (see FIG. 2) and through an aperture (not explicitly shown) defined through a first side of outer housing 116 of first shaft member 110 to enable engagement of one of the triggers 152. A second pivot boss 161b of crank 154 extends through an aperture (not explicitly shown) defined through a second side of outer housing 116 of first shaft member 110 to enable engagement of the other trigger 152 therewith, e.g., via press-fitting, adhesion, or other suitable engagement. As such, rotation of triggers 152 relative to first shaft member 110 drives rotation of crank 154 about first end portion 154a thereof.

Linkage 156 of knife deployment mechanism 150 includes a proximal end portion 156a pivotably coupled to a second end portion 154b of crank 154. A distal end portion 156b of linkage 156 is pivotably coupled to knife 140 via pivot pin 163. Pivot pin 163 may be integrally formed with linkage 156, e.g., as a post extending therefrom, or may be a separate component from linkage 156. Pivot pin 163 extends transversely through a longitudinal slot 115b of inner frame 114 such that pivot pin 163 is constrained to longitudinal movement within longitudinal slot 115b. Linkage 156 is disposed on one side of inner frame 114, which may be the same side as crank 154 or the opposite side (as shown). In either configuration, pivot pin 163 extends from linkage 156 and through longitudinal slot 115b, whereby a portion of pivot pin 163 protrudes laterally from the opposite side of inner frame 114. Knife 140 includes a proximal body 142 through which pin 163 extends transversely to pivotably couple knife 140 to distal end portion 156b of linkage 156.

First biasing member 158 of knife deployment mechanism 150 may be configured as an extension spring or other suitable biasing member 158a and is engaged at a distal end portion thereof to crank 154 and at a proximal end portion thereof to a support plate 166. Support plate 166 includes handle 118 of shaft member 110 integrally formed therewith or otherwise engaged thereto, and may be secured within outer housing 116 in any suitable fashion, e.g., via protrusion-aperture engagement. Support plate 166 provides increased structural support to first shaft member 110 to inhibit splaying of first and second shaft members 110, 120 during use. Second shaft member 120 similarly includes a support plate 168 integrally formed with or otherwise engaging handle 128 of shaft member 120 and secured to outer housing 126, although support plate 168 need not extend distally as with support plate 166.

Biasing member 158 biases crank 154 towards a first orientation, corresponding to the un-actuated position of triggers 152 and the proximal-most position of linkage 156, thereby biasing knife 140 towards the retracted position. Upon rotation of either of triggers 152 relative to first shaft member 110, crank 154 is rotated against the bias of biasing member 158 to thereby urge linkage 156 distally such that pivot pin 163 is driven distally though longitudinal slot 115b to urge knife 140 from the retracted position towards an extended position, in which knife 140 extends through pivot member 130 and jaw members 210, 220.

Second biasing member 160 of knife deployment mechanism 150 may be configured as an extension spring, compression spring, or any other suitable biasing member and is coiled about a distal body of knife 140. In some aspects, second biasing member 160 may be used in addition to or in place of first biasing member 158. In other aspects, biasing member 160 may be disposed about any suitable location of knife 140. Second biasing member 160 has a proximal end portion 160a disposed adjacent, and in some aspects, in contact with, a wall 147 of knife 140. A distal end portion 160b of biasing member 160 is disposed adjacent and in contact with pivot member 130, such that biasing member 160 is maintained between wall 147 of knife 140 and pivot member 130. In some aspects, distal end portion 160b of biasing member 160 may be disposed in contact with any other suitable component of first or second shaft members 110, 120, such as, for example, a clevis 125 of inner frame 124 of second shaft member 120.

Wall 147 of knife 140 protrudes from proximal body 142 of knife 140 and acts as a stop for the knife 140, inhibiting travel of knife 140 beyond the extended position. For example, upon knife 140 reaching the extended position, wall 147 of knife 140 may abut pivot member 130 rather than slide therethrough. Alternatively, rather than abutting pivot member 130, wall 147 of knife 140 may abut any other suitable portion of first or second shaft members 110, 120 to prevent further distal travel of knife 140 beyond the extended position.

In use, proximal end portions 112a, 122a of first and second shaft members 110, 120 are approximated, thereby moving end effector assembly 200 to the closed configuration. With end effector assembly 200 in the closed configuration, triggers 152 of knife deployment mechanism 150 are actuated (e.g., rotated in the direction indicated by arrow "A" in FIG. 1) with a force sufficient to overcome the proximally-oriented bias exerted on knife 140 by biasing member 160 and/or a force sufficient to overcome the proximally-oriented bias exerted by both first biasing member 158 on crank 154 and second biasing member 160 on knife 140. Second end portion 154b (FIG. 3) of crank 154 of knife deployment mechanism 150 rotates about first end portion 154a of crank 154. As crank 154 is rotated, linkage 156 of knife deployment mechanism 150 is translated distally and rotated about the pivotable coupling between proximal end portion 156a and second end portion 154b of crank 154. Since pivot pin 163 is supported by distal end portion 156b of linkage 156, pivot pin 163 translates in the direction indicated by arrow "B" in FIG. 3 upon rotation of linkage 156, which in turn translates knife 140 distally toward the extended position.

While knife 140 is translating distally in response to actuation of triggers 152, wall 147 of knife 140 distally urges proximal end portion 160a of second biasing member 160 toward distal end portion 160b of biasing member 160 to compress biasing member 160 between wall 147 of knife 140 and pivot member 130. Upon wall 147 of knife 140 approximating pivot member 130, or in some aspects contacting pivot member 130, pivot member 130 blocks further distal translation of knife 140.

To retract knife 140, the application of an actuation force on triggers 152 is ceased, allowing the proximally-oriented bias of now-compressed biasing member 160 to proximally urge knife 140 back toward the retracted position. In particular, proximal and distal end portions 160a, 160b of biasing member 160 push against wall 147 of knife 140 and pivot member 130, respectively, to translate knife 140 in the proximal direction. As knife 140 retracts, linkage 156 rotates to retract pivot pin 163. The rotation of linkage 156 rotates crank 154 and triggers 152 back to the un-actuated position, corresponding to the retracted position of the knife 140.

Figure 4:
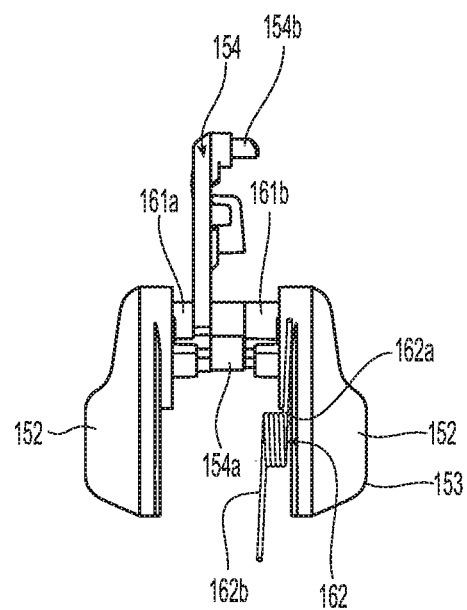
FIG. 4 is a front view of a pair of triggers attached to a crank of the knife deployment mechanism in accordance with further aspects of the present disclosure.

With respect to FIG. 4, in another aspect of the present disclosure, in addition to or in place of biasing members 158, 160 (FIG. 3), forceps 10 includes a biasing member 162 that directly applies a force on triggers 152 to resiliently bias triggers 152 toward the un-actuated position. Biasing member 162 is directly coupled to one of the triggers 152. In some aspects, two of biasing member 162 may be provided, one for directly applying a restoring force on each of the triggers 152. Biasing member 162 may be a torsion spring or any suitable biasing member (e.g., compression spring) and have a first end portion 160a attached to trigger 152, and a second end portion 162b fixed to inner frame 114. In some aspects, second end portion 162b of biasing member 162 may be fixed to any suitable location of first or second shaft members 110, 120 (FIG. 1), such as, for example, outer housing 126 of second shaft member 120. Biasing member 162 exerts a generally distally-oriented force on an end portion 153 of trigger 152. In this embodiment or in all embodiments, crank 154 and triggers 152 may be monolithically formed with one another.

In use, proximal end portions 112a, 122a of first and second shaft members 110, 120 are approximated, thereby moving end effector assembly 200 to the closed configuration. With end effector assembly 200 in the closed configuration, triggers 152 of knife deployment mechanism 150 are actuated (e.g., rotated in the direction indicated by arrow "A" in FIG. 1) with a force sufficient to overcome the bias directly exerted on trigger 152 by biasing member 162 and/or a force sufficient to overcome the bias exerted by first biasing member 158 on crank 154, second biasing member 160 on knife 140, and third biasing member 162 on trigger 152. Second end portion 154b (FIG. 3) of crank 154 of knife deployment mechanism 150 rotates about first end portion 154a thereof. Rotation of crank 154 rotates and translates linkage 156 of knife deployment mechanism 150. Since pivot pin 163 is supported by distal end portion 156b of linkage 156, pivot pin 163 translates in the direction indicated by arrow "B" in FIG. 3 upon rotation of linkage 156, which in turn translates knife 140 distally toward the extended position. Ceasing the application of an actuation force on triggers 152 allows the bias of now-compressed biasing member 162 to rotate triggers 152 in the opposite direction, namely the direction indicated by arrow "C" in FIG. 3, in a similar manner as described above.

For an additional description of various components and manners of operating forceps 10 of the present disclosure, reference may be made to U.S. patent application Ser. No. 15/593,672, filed on May 12, 2017, the entire contents of which are incorporated herein by reference.

The various embodiments disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients.

For a detailed description of exemplary medical work stations and/or components thereof, reference may be made to U.S. Patent Application Publication No. 2012/0116416 (now U.S. Pat. No. 8,828,023), and PCT Application Publication No. WO2016/025132, the entire contents of each of which are incorporated herein by reference.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical forceps, comprising:
a pair of first and second shaft members pivotably coupled to one another;
an end effector assembly coupled to the pair of first and second shaft members and configured to pivot about a pivot member between an open configuration and a closed configuration in response to pivoting of the first and second shaft members;
a knife selectively translatable through the first shaft member from a retracted position to an extended position in which the knife extends at least partially through the end effector assembly, the knife having a wall projecting outwardly therefrom; and
a biasing member disposed about the knife and configured to resiliently bias the knife toward the retracted position, the biasing member being positioned between the pivot member and the wall of the knife.

2. The electrosurgical forceps according to claim 1, wherein the biasing member is an elongated spring wrapped around the knife.

3. The electrosurgical forceps according to claim 1, wherein the biasing member is compressed between the wall of the knife and the pivot member during distal translation of the knife toward the extended position.

4. The electrosurgical forceps according to claim 3, wherein the wall is a stop engaged to a proximal end portion of the biasing member and configured to resist distal translation of the knife beyond the extended position.

5. The electrosurgical forceps according to claim 1, wherein the biasing member has a proximal end portion engaged to the wall of the knife, and a distal end portion engaged to the pivot member.

6. The electrosurgical forceps according to claim 1, further comprising a knife deployment mechanism including:
a linkage having a proximal end portion operably coupled to a trigger; and
a pivot pin rotatably supported by a distal end portion of the linkage and coupled to the knife, wherein the knife is configured to move between the retracted and extended positions in response to an actuation of the trigger.

7. The electrosurgical forceps according to claim 6, wherein the knife deployment mechanism includes a crank having a first end portion coupled to the trigger and a second end portion rotatably coupled to the proximal end portion of the linkage.

8. The electrosurgical forceps according to claim 7, wherein the crank rotates in response to an actuation of the trigger to rotate and translate the linkage.

9. An electrosurgical forceps, comprising:
a pair of first and second shaft members pivotably coupled to one another;
a trigger rotatably supported by at least one of the first or second shaft members and configured to move relative to the at least one of the first or second shaft members between an unactuated position and an actuated position;
an end effector assembly coupled to the pair of first and second shaft members and configured to move between an open configuration and a closed configuration in response to pivoting of the first and second shaft members;
a knife selectively translatable through the first shaft member from a retracted position to an extended position in which the knife extends at least partially through the end effector assembly;
a knife deployment mechanism including a crank having a first end portion coupled to the trigger and a second end portion operably coupled to the knife;
a first biasing member coupled to the trigger and configured to resiliently bias the trigger toward the unactuated position; and
a second biasing member disposed about the knife and configured to resiliently bias the knife toward the retracted position.

10. The electrosurgical forceps according to claim 9, wherein the first biasing member has a first end portion attached to the trigger and a second end portion fixed to a portion of at least one of the first or second shaft members.

11. The electrosurgical forceps according to claim 10, wherein the first shaft member has an outer housing and an inner frame disposed within and axially fixed relative to the outer housing, the trigger rotatably supported by the inner frame.

12. The electrosurgical forceps according to claim 11, wherein the second end portion of the first biasing member is fixed to the inner frame.

13. The electrosurgical forceps according to claim 9, wherein the first biasing member is a torsion spring.

14. The electrosurgical forceps according to claim 9, wherein the knife deployment mechanism includes a linkage having a proximal end portion operably coupled to the trigger, and the knife is configured to move between the retracted and extended positions in response to an actuation of the trigger.

15. The electrosurgical forceps according to claim 14, wherein the knife deployment mechanism includes a pivot pin rotatably supported by a distal end portion of the linkage and coupled to the knife.

16. The electrosurgical forceps according to claim 14, wherein the crank rotates from an unactuated position to an actuated position in response to an actuation of the trigger to rotate the linkage and move the knife between the retracted and extended positions.

17. The electrosurgical forceps according to claim 16, further comprising a third biasing member coupled to the crank and configured to resiliently bias the crank to the unactuated position.

* * * * *